United States Patent [19]

Matsumura et al.

[11] Patent Number: 6,153,400
[45] Date of Patent: Nov. 28, 2000

[54] DEVICE AND METHOD FOR MICROBIAL ANTIBIOTIC SUSCEPTIBILITY TESTING

[75] Inventors: Paul M. Matsumura, Cary; Jones M. Hyman, Durham; Scott R. Jeffrey, Raleigh; Martin J. Maresch; Thurman C. Thorpe, both of Durham; William G. Barron, Bahama, all of N.C.

[73] Assignee: Akzo Nobel N.V., Arnhem, Netherlands

[21] Appl. No.: 09/267,863

[22] Filed: Mar. 12, 1999

[51] Int. Cl.[7] .............................. C12Q 1/18; C12Q 1/04; C12M 1/22; C12M 1/00

[52] U.S. Cl. .................. 435/32; 435/34; 435/4; 435/305.1; 435/305.2; 435/305.3; 435/289.1; 435/283.1; 435/287.1; 435/288.3; 435/288.4

[58] Field of Search ........................ 435/32, 34, 4, 435/305.1, 305.2, 305.3, 289.1, 283.1, 287.1, 288.3, 288.4

[56] References Cited

U.S. PATENT DOCUMENTS

| | | | |
|---|---|---|---|
| 3,272,710 | 9/1966 | Avakian | 435/32 |
| 3,715,280 | 2/1973 | Farmer, III | 435/32 |
| 4,055,470 | 10/1977 | Hinton et al. | 435/32 |
| 4,090,920 | 5/1978 | Studer, Jr. | 435/32 |
| 4,252,904 | 2/1981 | Nelson et al. | 435/32 |
| 4,701,850 | 10/1987 | Gibbs | 435/32 |
| 5,344,761 | 9/1994 | Citri | 435/32 |

FOREIGN PATENT DOCUMENTS

| | | |
|---|---|---|
| 8803814 | 2/1988 | Brazil . |
| 0 576 753 A1 | 7/1992 | European Pat. Off. . |
| 2250439 | 12/1973 | France . |
| 2331992 | 11/1974 | France . |
| 2367825 | 11/1975 | France . |
| 2698702 | 2/1992 | France . |
| 2344380 | 5/1982 | Germany . |
| 3336738 | 8/1983 | Germany . |
| 2001105 | 1/1987 | Russian Federation . |
| 1596154 | 10/1976 | United Kingdom . |
| WO 98/53301 | 11/1998 | WIPO . |

OTHER PUBLICATIONS

Jorgensen, J.H., *Selection Criteria for the Antimicrobial Susceptibility Testing System*, Jour. Of Clinical Mirobiology, Nov. 1993, pp. 2841–2844.

Jorgensen, J. et al., *Antimicrobial Susceptibility Testing: General Principles and Contemporary Practices*, Clinical Infectious Diseases, 1998; 26:973–80.

U.S. Food and Drug Administration Center for Food Safety and Applied Nutrition, "Milk Monitoring with Antimicrobial Drug Screening Tests", Center for Veterinary Medicine Update, Jan. 25, (1996).

Richardson, G.H., *Standard Methods for the Examination of Dairy Products*, 15$^{th}$ Ed. 1985, pp.275–279.

*Performance Standards for Antimicrobial Disk Susceptibility Tests–Sixth Edition; Approval Standard*, National Committee on Clinical Laboratory Standards, vol. 17. No. 1, (1998).

(List continued on next page.)

*Primary Examiner*—Louise N. Leary
*Attorney, Agent, or Firm*—Gregory R. Muir

[57] ABSTRACT

A method and apparatus for performing microbial antibiotic susceptibility testing include disposable, multi-chambered susceptibility plates and an automated plate handler and image acquisition and processing instrument. The susceptibility plates are inoculated with a microorganism (any suitable organism such as bacteria, fungi, protozoa, algae or viruses) and anti-microbial agent(s) are applied such that the microorganism is exposed to a variety of concentrations, or a gradient of each anti-microbial agent. The plates are then placed in the instrument, which monitors and measures the growth (or lack thereof) of the microorganisms. This data is used to determine the susceptibility of the microorganism to the antibiotics. Such a system automates antimicrobial susceptibility testing using solid media and Kirby-Bauer standardized result reporting. The system provides a level of automation previously associated only with broth microdilution testing, while retaining the advantages of the manual disk diffusion test.

49 Claims, 11 Drawing Sheets

OTHER PUBLICATIONS

Koletar, S.L., *Concepts in Anitmicrobial Therapy*, Chapter 3, pp.5–96, (1997).

"AutoAssay®Systems", product information, (1998).

*New Test Method Developed for Detecting Drug Residues*, USDA ARS Quarterly Report, (Jan.–Mar. 1995).

Jones, G.M. et al., *On–Farm Tests for Antibiotic Residues*, (1997).

"Delvotesto P MINI", product information, (1997).

Hill, G.B., *J. Clin. Microbio.* 29 (1991) No. 5, pp. 975–979.

Hill, G.B. et al., *Rev. Infect. dis.*, 12 (1990) Suppl. 2, S200–S209.

Master, P.J., et al., *J. Appl. Bacteriol.*, 51 (1981) No. 2, 253–255.

Schmieger, H., *Prax. Maturwiss.* Biol. 29 (1980) No. 9, 278–280.

Reeves, D.S., et al., *Anitmicrob. Agents Chemother.*, 18 (1980) No. 6, 844–852.

Dougherty, P.F. et al., *Antimicrob., Agents Chemother.* 11 (1977) No. 2, 225–258.

Joly–Guillou, M.L. et al., *Pathol. Biol.*, 35 (1987) No. 5, 563–567.

Le Noc, P., et al., *Pathol. Biol.*, 33 (1985) No. 9, 906–910.

Boucaud–Maitre, Y., et al., *Pathol. Biol.*, 44 (1996) No. 5, 363–366.

Christensen, JJ, et al. *J. Antimicrobial Chemother.*, 38, (1996) No. 2, 253–258.

Chang, J.C., et al., *Anitmicrob. Agents Chemother.*, 41 (1997) No. 6, 1301–1306.

Marco, F., et al., *Diagnost. Microbiol. Infect. Dis.*, 29(1997) No. 1, 55–57.

Dyck E. van, et al., *J. Clinical Microbiol.* 32 (1994) No. 6, 1586–1588.

Shapiro, M.A. et al., *J. Clinical Microbiol.* 20, (1984) No. 4, 828–830.

Chernomordick, AB et al., *Antibiotiki*, 25 (1980) No. 11, 834–337.

DEVICE AND METHOD FOR MICROBIAL ANTIBIOTIC SUSCEPTIBILITY TESTING

BACKGROUND OF THE INVENTION

Following detection of a microorganism in a patient sample, it is often desirable to determine to which antibiotics the microorganism is susceptible. There are now a number of bacterial species which increasingly exhibit resistance to one or more classes of antimicrobial agents, making it that much more important to perform susceptibility testing. Failure of a particular susceptibility test to accurately predict antimicrobial resistance in a patient's isolate could significantly impact patient care if an antibiotic is used to which the microorganism is not susceptible.

Different types of susceptibility tests can be used to test a microorganism. The following brief descriptions give details of some known susceptibility tests as well as some details that relate to the present invention.

Figure 1:
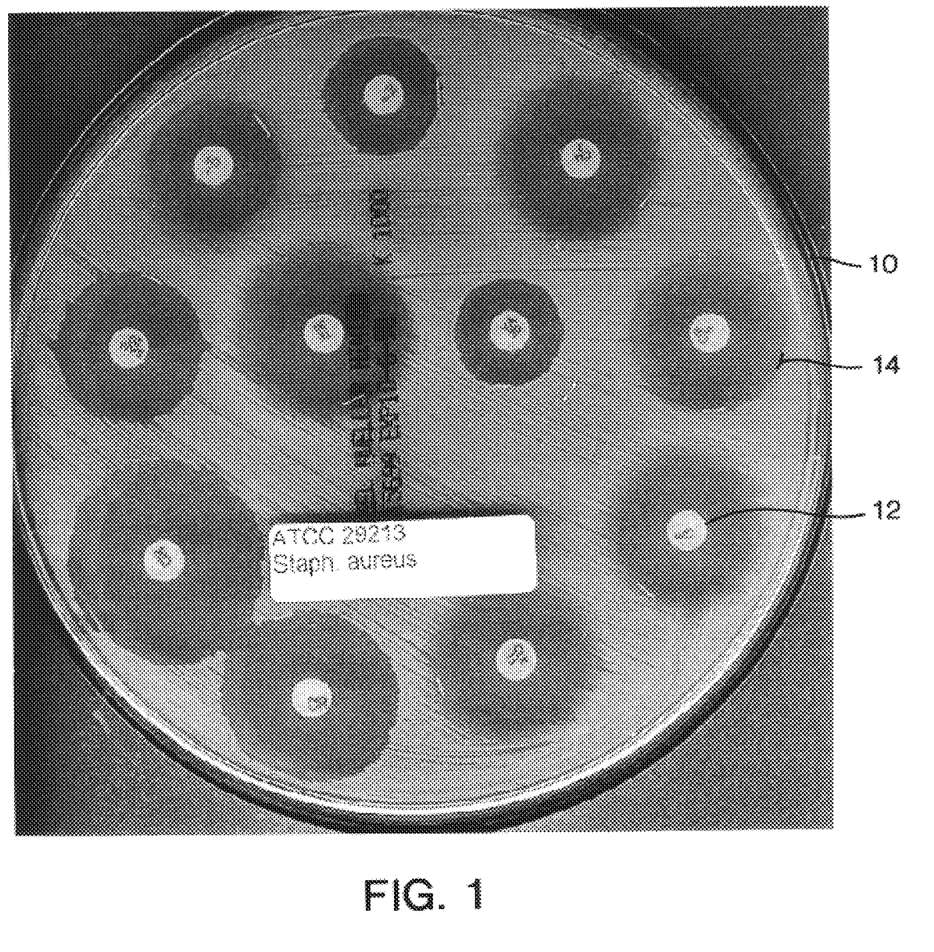
FIG. 1 is an illustration of an agar plate for performing a disk diffusion antibiotic susceptibility test.

One type of susceptibility test is the disk diffusion test, often referred to as the Kirby-Bauer test. This is a standardized test that involves inoculating (with 0.5 McFarland standardized suspension of a microbial isolate) a gel plate (e.g. a 150-mm Mueller-Hinton agar plate) and placing thereon one or more disks impregnated with fixed concentrations of antibiotics. After incubation (e.g. 18–24 hours at 35 degrees C), the diameter of zones of inhibition around the disks (if present) determine the sensitivity of the inoculated microorganism to the particular antimicrobial agent impregnated in each disk. Due to the standardization of the Kirby-Bauer method, results of this method are analyzed by comparing the diameter of the inhibition zone with information published by NCCLS (National Committee on Clinical Laboratory Standards) in *Performance Standards for Antimicrobial Disk Susceptibility Testing*, the subject matter of which is incorporated herein by reference. The results of this test are semi-quantitative in that there are three categories of susceptibility—namely resistant, intermediate and susceptible. As can be seen in FIG. 1, an agar plate 10 with inoculum has a plurality of disks 12 placed thereon, which disks are impregnated with antibiotics (of different types and/or concentrations). After incubation, zones of microbial growth inhibition 14 are formed. These zones 14 are interpreted to be resistant, intermediate or susceptible based on NCCLS criteria.

Figure 2:
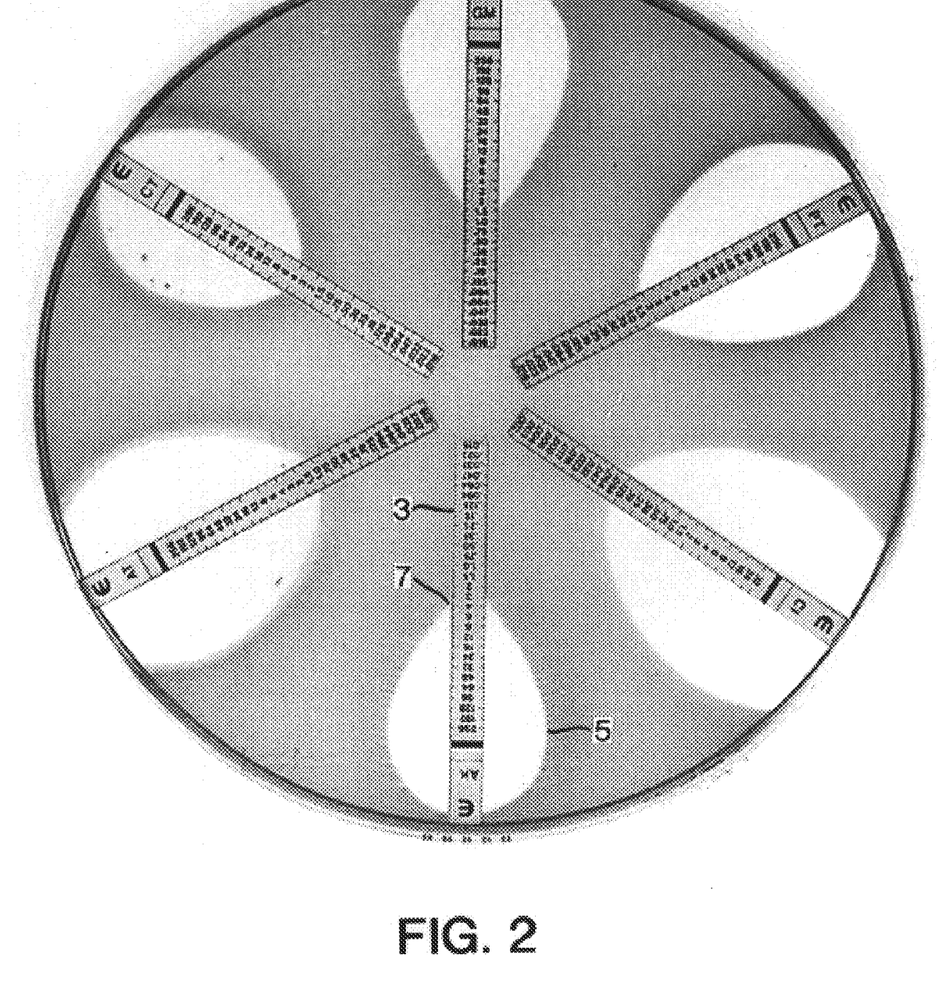
FIG. 2 is an illustration of an antibiotic gradient method for determining susceptibility of a microorganism to particular antimicrobial agents.

Another method of antimicrobial susceptibility testing is the antibiotic gradient method. This test utilizes an antibiotic gradient in a gel medium. Paper or plastic strips are impregnated with an antibiotic concentration gradient. A plurality of strips are placed on a Mueller-Hinton agar plate like spokes on a wheel, with the plate having been inoculated with the microorganism to be tested. After incubation, an antibiotic gradient is formed in the gel in an elliptical shape around each test strip (if the microorganism is susceptible to the antibiotic on the particular strip). The minimum concentration of the antimicrobial agent that prevents visible microorganism growth is the endpoint of the test (the minimum inhibitory concentration, or MIC). Put in other words, in disk diffusion testing, the MIC is the concentration at the edge of the inhibition zone (the growth/no growth boundary). In this case, the MIC is the point at which the elliptical growth inhibition area intersects the test strip. As can be seen in FIG. 2, agar plate 1 has a plurality of test strips 3 that are impregnated with an antibiotic gradient. Elliptical zones 5 are formed where microorganism growth is inhibited by the antibiotic agent in/on the test strip. Point 7 where the elliptical zone intersects the test strip is the MIC point.

A third type of susceptibility test is the broth microdilution test. In this type of test, dilutions of antibiotics (e.g. consecutive two-fold dilutions) are prepared. Often, at least ten concentrations of a drug are prepared in tubes or microwells. Each tube or well having the various concentrations of antibiotics is inoculated with a particular microorganism (a standardized suspension of test bacteria is added to each dilution to obtain a final concentration of $5 \times 10^5$ CFU/ml). A growth control well and an uninoculated control well are included on each plate. After incubation (e.g. for 16–24 hours at 35 degrees C), the wells or tubes are examined manually or by machine for turbidity, haze and/or pellet. Indicators can be placed in the wells to facilitate the visualization of microbial growth. As with other tests, the minimum concentration of antimicrobial agent that prevents visible microbial growth is the MIC.

Figure 3:
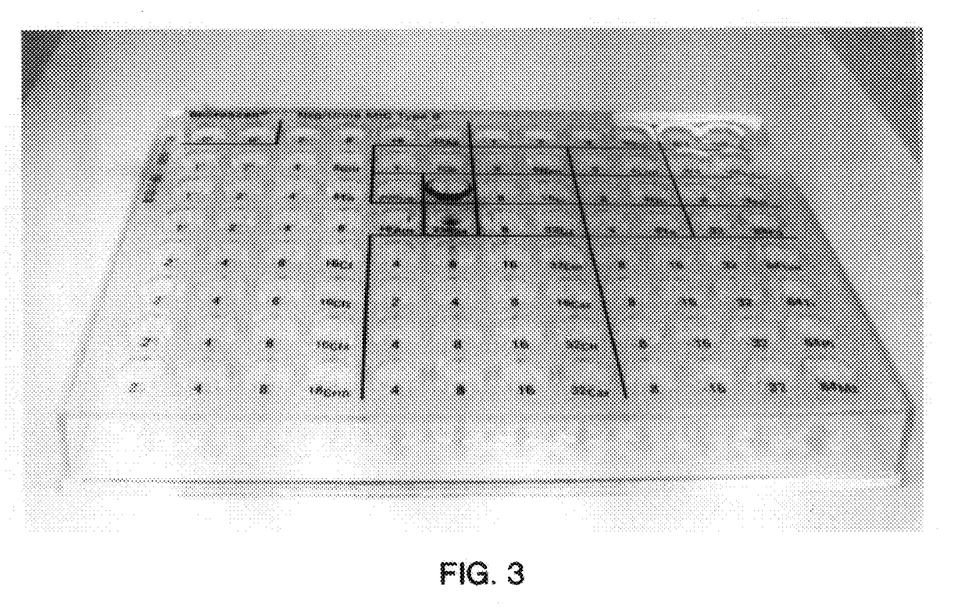
FIG. 3 is an illustration of a device for performing a broth microdilution antibiotic susceptibility test.

Commercial microdilution tests are typically performed on standard 96 well plates, each well holding approximately 100 to 200 microliters with commercially prepared antibiotic test panels. With 96 wells and 2 to 10 different dilutions for each antibiotic, numerous antibiotics can be tested on a single plate. A significant problem with such commercial microdilution systems is the inflexibility of the standard antibiotic test panels. The commercial plates are manufactured with various amounts of frozen, dried or lyophilized antimicrobial agents in the wells. This avoids the time consuming task of preparing the plates. However, due to the availability of many antibiotics (more than fifty in the United States), it is often problematic for a laboratory to find a standard commercial test panel which is ideal for that laboratory's needs. FIG. 3 is an illustration of a 96-well plate used in such a microdilution system.

A variation of the broth microdilution method is set forth in U.S. Pat. No. 5,501,959. This system uses microtiter plates with 168 wells, each containing a paper disk attached to the bottom of the well. The disks contain serial two-fold dilution concentrations of various antimicrobial agents, as well as a redox indicator. Up to 20 different antimicrobial agents can be tested on a plate. This use of paper disks simplifies the manufacture of the custom panels. However, higher costs are involved when a susceptibility test is custom made for a customer.

Current instruments that offer the highest degree of automation in susceptibility testing are typically based on automating the tasks performed in the manual broth microdilution method mentioned above. One such example is the instrument described in U.S. Pat. No. 4,448,534. This instrument uses multi-well plates that are pre-loaded with serial two-fold dilution concentrations of antimicrobial agents. Plates are inoculated manually and placed in the instrument, where they are incubated. At the appropriate times, the wells on the plate are read by a photometer/fluorometer to determine the results of the test. Another automated system is described in U.S. Pat. No. 3,957,583. This instrument uses small multi-chamber cards that are pre-loaded with serial two-fold dilution concentrations of antimicrobial agents. Cards are inoculated automatically, incubated, and monitored within the instrument. This instrument reads the chambers in the card periodically using a photometer. These kinetic measurements yield growth curves that allow the instrument to determine the results of the test. Though the aforementioned instruments perform testing in 4 to 8 hours, they may fail to detect induced resistance of the microorganism, which could result in an incorrect susceptibility report. Unfortunately, the degree of automation that is provided by instruments based on broth microdilution is not available for methods such as disk diffusion.

SUMMARY OF THE INVENTION

The present invention relates to a system for performing microbial antibiotic susceptibility testing. The system is comprised of disposable, multi-chambered susceptibility plates and an automated plate handler and image acquisition and processing instrument. The susceptibility plates are inoculated with a microorganism (any suitable organism such as bacteria, fungi, protozoa, algae or viruses) and anti-microbial agent(s) are applied such that the microorganism is exposed to a variety of concentrations, or a gradient of each anti-microbial agent. The plates are then placed in the instrument, which monitors and measures the growth (or lack thereof) of the microorganisms. This data is used to determine the susceptibility of the microorganism to the antibiotics. Such a system automates antimicrobial susceptibility testing using solid media and Kirby-Bauer standardized result reporting. Thus, the present invention provides a level of automation previously associated only with broth microdilution testing, while retaining the advantages of the manual disk diffusion test.

BRIEF DESCRIPTION OF THE DRAWINGS

FIGS. 5a and 5b are top views of two embodiments of the invention where FIG. 5a illustrates elongated channels with antibiotic disks, and where FIG. 5b illustrates shorter channels, some with antibiotic disks therein;

FIG. 6a illustrates an embodiment with elongated channels each having an antibiotic strip therein, whereas

FIGS. 7a and 7b are views of a susceptibility plate with *E. coli*, where FIG. 7a shows a raw image and FIG. 7b shows a processed image;

FIGS. 8a and 8b are views of a susceptibility plate with *S. aureus*, where FIG. 8a shows a raw image and FIG. 8b shows a processed image;

FIGS. 9a to 9d are additional views of a susceptibility plate for *Kleb. pneumoniae*, where FIG. 9a is an unprocessed image after 4 hours, FIG. 9b is a processed image after 4 hours, FIG. 9c is an unprocessed image after 18 hours, and FIG. 9d is a processed image after 18 hours.

DETAILED DESCRIPTION OF THE PREFERRED EMBODIMENT

Figure 4:
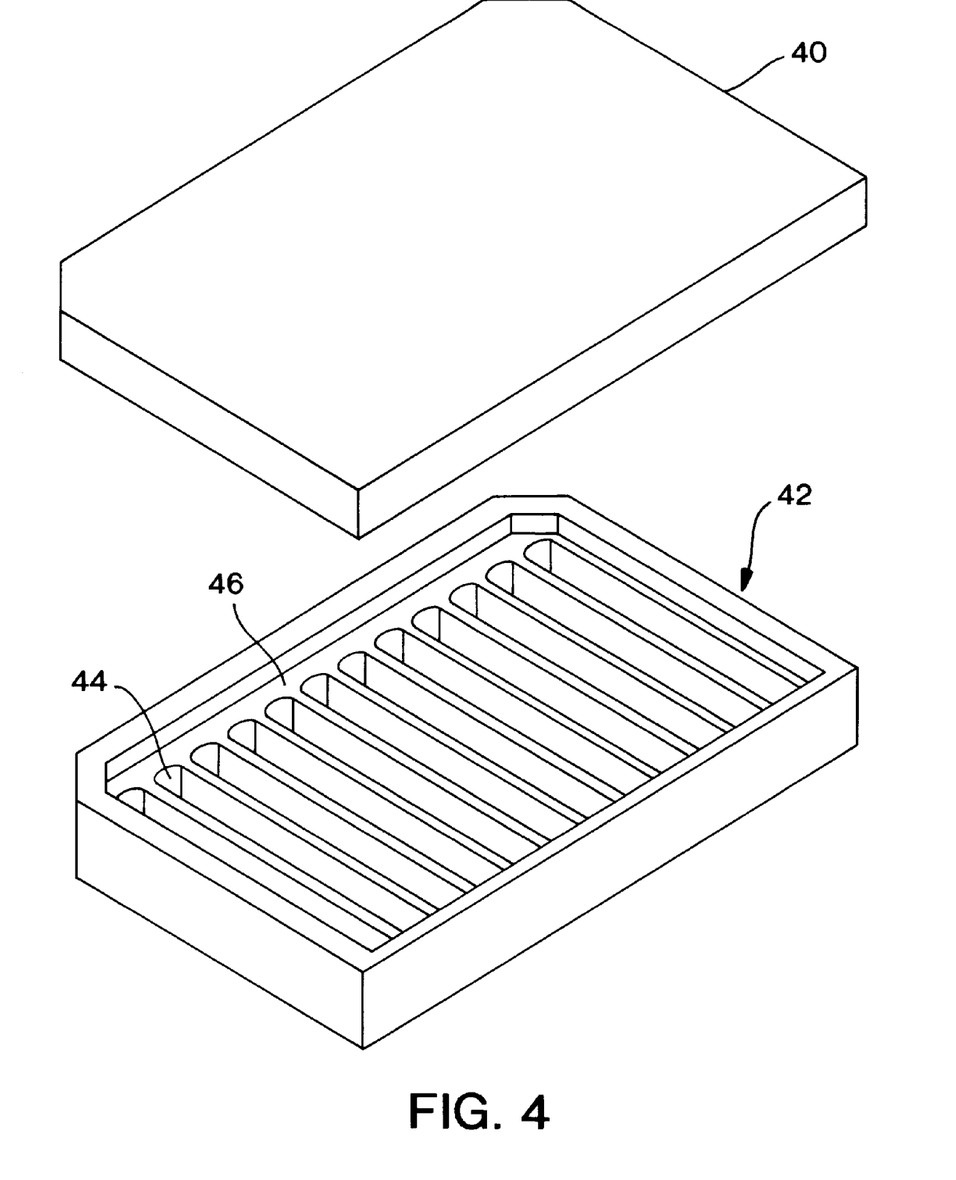
FIG. 4 is an illustration of one embodiment of the present invention having a bottom portion with a bottom gel plate having internal partitions, and a top cover.

One embodiment of the susceptibility plate of the present invention is illustrated in FIG. 4. Such a plate is provided to be disposable and have a low cost for manufacture, and is preferably made of plastic. A top 40 is provided which fits onto bottom 42. Top 40 is preferably transparent or otherwise having properties that can allow viewing (manually or with machine) of microbial growth in the channels in bottom 42. Bottom 42 is provided with a plurality of channels 44 or otherwise mutually isolated chambers. Such channels can be formed within an insert 46 that fits into bottom 42, or bottom 42 and insert 46 can be integrally formed as a single piece (and either or both of the bottom and insert can be opaque). Preferably, marks such as those illustrated along each channel in FIGS. 5 and 6 (or other markings such as numbers) are provided for aiding in manual measurement of the length of inhibition in the channel, if such is desired. This is a definite advantage compared to the standard manual disk diffusion system, where calipers are used to measure a diameter of the inhibition zone, a system that is more labor intensive and less accurate. Each channel 44 contains a growth medium that is solid (or semi-solid). Such growth medium may optionally contain an indicator additive for improving the readability of growth patterns in the various channels. Also, an indicator may be provided in a separate layer (a "sensor layer"), a conditioning layer may be provided, and various components can be provided in the gel layer, such as described in U.S. patent application 08/989,560, filed Dec. 12, 1997, the subject matter of which is incorporated herein by reference.

Figure 5A:
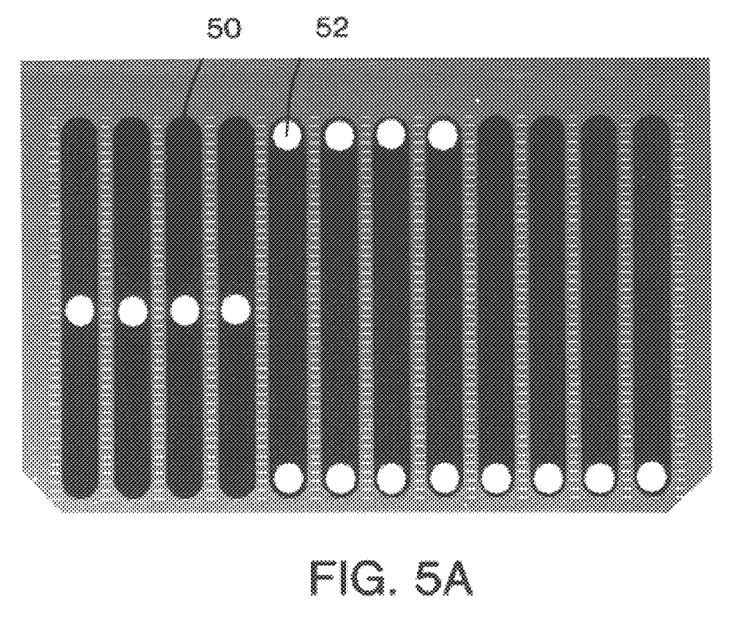
Figure 5B:
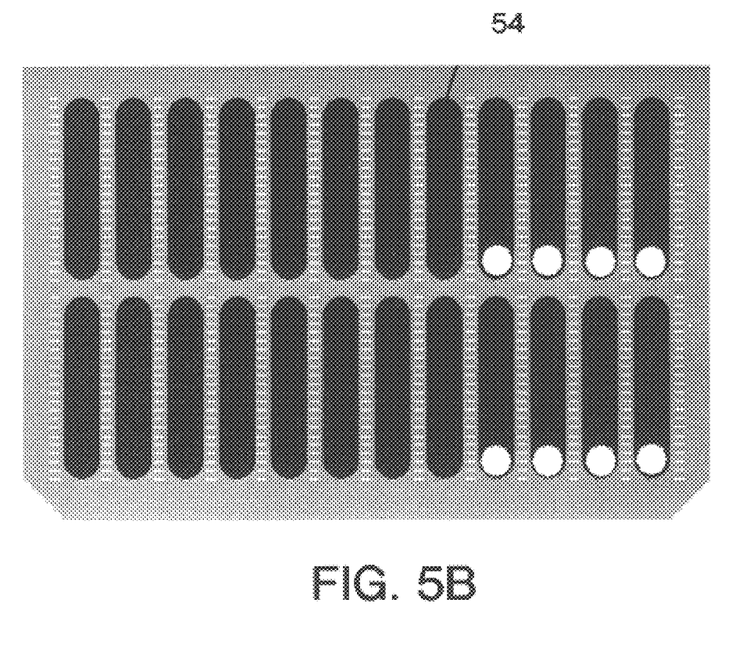
Figure 6A:
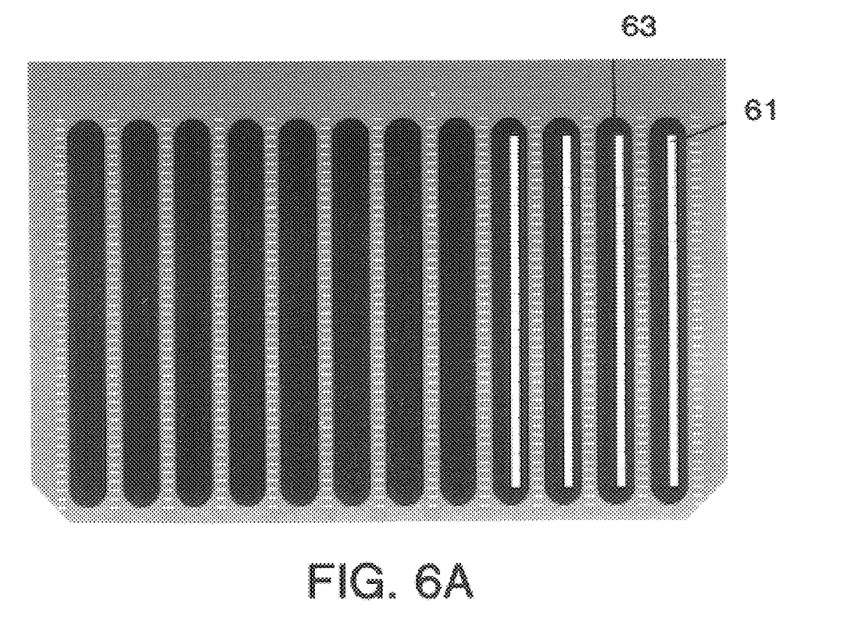
Figure 6B:
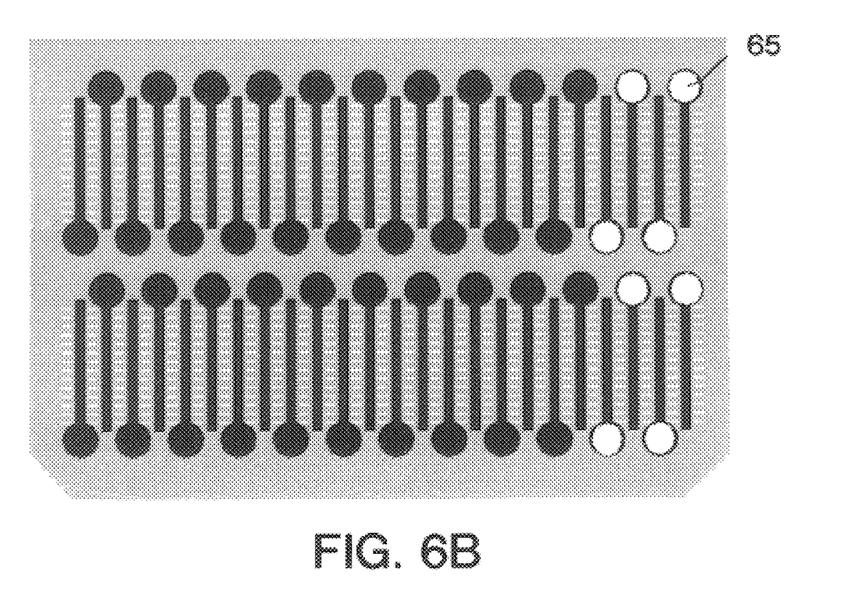
FIG. 6b illustrates an embodiment having thin shorter channels with antibiotic disks at one end thereof.

Physically, the external geometry of the susceptibility plate could be made similar to that of a standard microwell plate (128 mm×86 mm). However, other shapes and sizes are envisioned. The plate could be made to be almost any geometric shape, including square or even round like a standard agar plate. Whatever the external geometry, internally the plate is partitioned into separate chambers or channels in which the solid (or semi-solid) medium is held. The wells or chambers within the plate are preferably elongated channels, though triangular, pie-shaped, circular or square wells, or other geometrically shaped wells, are also envisioned. As an example, FIG. 5a illustrates one embodiment where mutually isolated channels 50 extend almost fully across the width of the plate. Antibiotic disks 52 are placed in each channel at the end or middle of the channel. Shorter channels 54 could also be formed in the plate, such as those illustrated in FIG. 5b. FIG. 6a illustrates a further example where antibiotic gradient strips 61 are disposed in elongated channels 63. In this embodiment, an MIC (minimum inhibitory concentration) can be determined (the MIC is the concentration at the edge of the inhibition zone—the growth/no growth boundary). The separated channels could also be made much narrower, such as illustrated in FIG. 6b. However, if it is desired to use standard antibiotic disks 65 such as those commercially provided for standard Kirby-Bauer antibiotic testing (which disks are approximately 6 mm in diameter), then larger antibiotic disk receiving areas should be provided, such as at the end of each narrow channel. Generally, the channel length is greater than 8 mm (preferably from 20 mm to 45 mm in length), and the channel width is greater than 6 mm (preferably from 8 mm to 16 mm in width). A channel width of approximately 8 mm is most preferred if standard antibiotic disks are used (which are approximately 6 mm in diameter). Of course, if antibiotic disks of different size are used, the channel dimensions could be made larger or smaller. A length of from about 30 to 35 mm is most preferred as this allows sufficient length to detect and measure inhibition zones resulting from nearly all antibiotic/microorganism combinations used in susceptibility testing. The depth of the solid or semi-solid growth medium in the channels should be more than 1 mm, preferably from about 2 mm to about 20 mm, and more preferably from about 5 mm to about 15 mm.

One of the purposes of the isolated chambers is to increase the ease and reproducibility of susceptibility testing, as well as to maximize the number of tests that can be performed on one susceptibility plate. Whereas standard disk diffusion (Kirby-Bauer) tests are physically restricted to a density of 12 tests or less per 150-mm Mueller-Hinton plate (one test per 14.73-cm$^2$), the present invention easily allows for 24 tests or more on a 128 mm×85 mm plate (at least one test per 4.53-cm$^2$), a density of more than 3 times that of the standard disk diffusion plate. Initially it was thought that the length of inhibition area in a channel in the present invention would not correlate with the radius of inhibition on a standard disk diffusion plate (when using the same microorganism and antibiotic). Instead, it was found that the measured length of inhibition was substantially the same in the present invention as the radius measured in the standard plate. By "substantially the same" it is meant that the measured lengths in the present invention and in a standard Kirby-Bauer test after the same period of time were either exactly the same, or close enough that the ultimate outcome of the test (susceptible, intermediate or resistant as defined by the National Committee for Clinical Laboratory Standards, or NCCLS) correlated over 80% of the time, and were within the control ranges outlined by the NCCLS. In most cases the results correlated over 90% of the time. And, in only in a small percentage (<1.1%) of cases did the results of the present invention indicate susceptible when the standard Kirby-Bauer test (with same microorganism and antibiotic) indicated resistant, or vice-versa (<0.9%).

The susceptibility plates of the present invention are used as follows:

1) Disks containing single concentrations, or strips containing several concentrations, of each antibiotic being tested are placed (manually or automatically) onto the inoculated surface of the growth medium in each chamber of the susceptibility plate. Once the disks or strips are placed on the plate, the antibiotics start to diffuse into the growth medium forming an antibiotic gradient within the growth medium. Antibiotic panels are flexible and can be user-configurable and/or pre-configured.

2) The susceptibility plate is placed in the instrument (manually or automatically) where it is incubated, promoting the growth of microorganisms within the chambers, except where inhibited by antibiotics diffused into the growth medium.

3) The susceptibility plate is inspected manually or automatically to determine the presence and length of inhibition zones in the chambers. Ruler markings or numberings along each channel facilitates manual zone measurements. Automatic zone measurements are performed by the instrument via image capture and image processing.

As mentioned above, the length of the inhibition in the channel of the susceptibility plate can be measured manually, or automatically. If automatically, an instrument is provided which is responsible for performing three main functions: susceptibility plate incubation, image acquisition/capture, and image processing. The instrument provides a controlled environment to incubate the plates. Susceptibility plates are inoculated and placed in the incubator where they are subsequently scanned by an image acquisition device during the incubation period. The instrument provides for image acquisition using one or more color and/or gray scale imaging devices: CCD linear array scanner, a CCD line-scan camera, a CCD 2D array camera (still or motion video), a laser scanning camera, or other device that would provide a sufficiently clear image of the susceptibility plate that can be used alone or after further processing. By "image" it is meant any information, such as optical information, from the susceptibility plate that is $\geq$ a 1×1 pixel. The image acquisition is performed at regular pre-programmed intervals, with the captured image obtained from one or more views and angles of the susceptibility plate.

Figure 10:
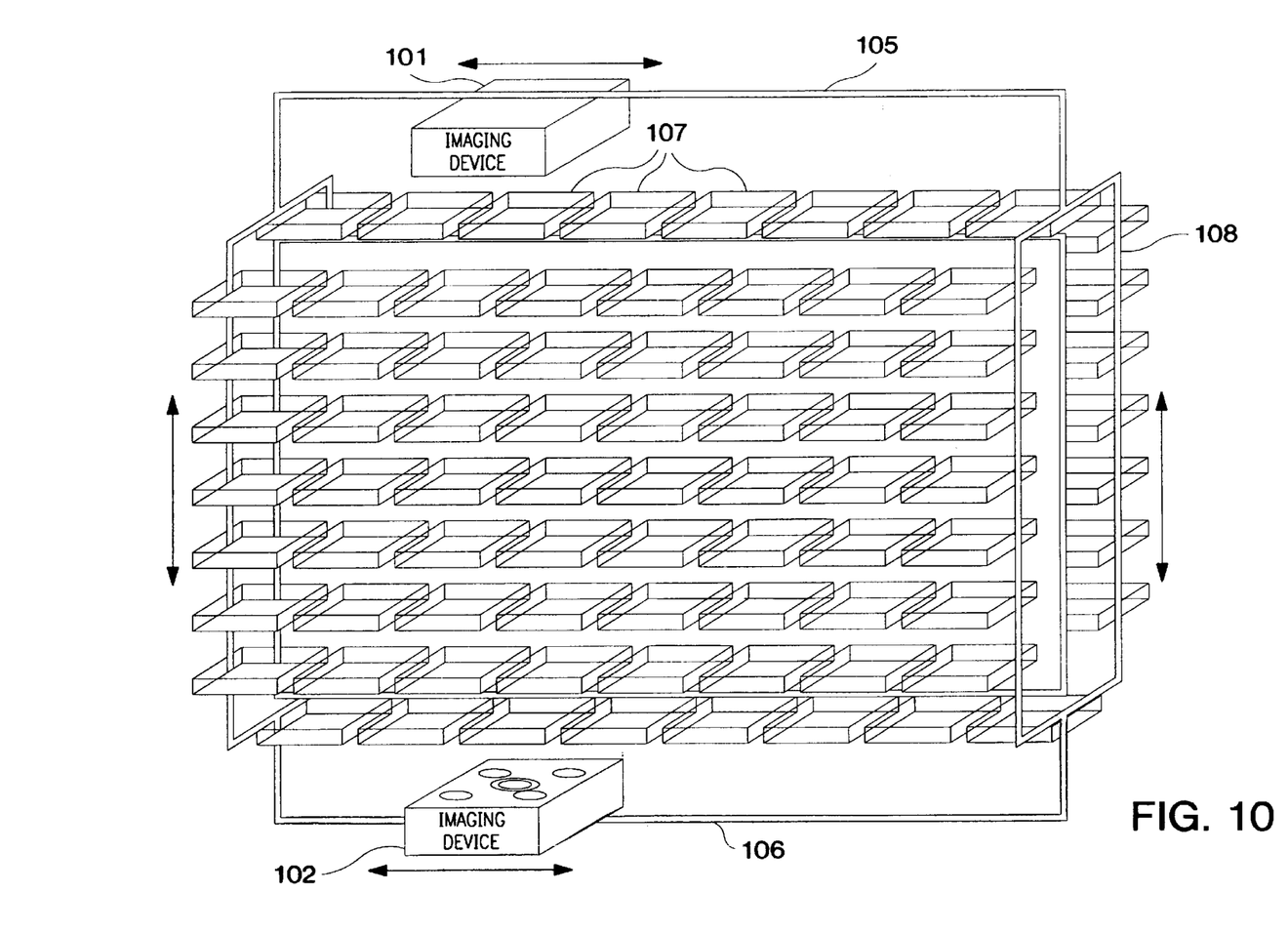
FIG. 10 is an illustration of one system for moving a plurality of susceptibility plates past imaging devices for detecting and processing images of the plates.

One example of how susceptibility plates could be moved relative to one or more imaging devices is illustrated in FIG. 10. As can be seen in this figure, imaging devices 101 and 102 are provided for capturing the image of the top and bottom, respectively, of each susceptibility plate. Top and bottom imaging transport systems 105 and 106 are provided for moving the respective imaging devices past a plurality of plates when the plates are disposed at the top or bottom imaging station. Each susceptibility plate 107 at each imaging station has its image captured by an imaging device. Susceptibility plates are moved to the imaging stations by a plate transport system 108 that, as in FIG. 10, moves plates both upwardly and downwardly from the imaging stations. Of course other plate and/or imaging device transport systems could be utilized. A cartridge system could be used, where one plate at a time is removed from a stack for imaging (and either the stack or imaging device is moved to position the imaging device and selected plate in proximity to each other). A turntable or other rotary system could be used to position each plate proximate to an imaging device, or a conveyor belt or wheel system could be used, where plates (with solid media) are affixed to a belt or wheel in rows and are turned upside down depending upon which side of the belt or wheel the plate is on.

Images acquired during the incubation period are analyzed using one or more image processing techniques. In the example of FIG. 10, images are acquired from both the top and bottom of the plate at regular intervals (though imaging only one side of the plate is also envisioned). Typically the interval is from 5 minutes to 4 hours, though preferably the interval is between one half-hour and 2 hours, and most preferably every hour. Scanning at regular intervals provides kinetic growth data, which may be used to help characterize the microorganisms. The image-processing algorithm implemented to determine susceptibility is comprised of one or more of the following steps:

a) Image Masking—to isolate the area of interest from extraneous image data;

b) Antibiotic Disk or Strip Detection—to determine identity and concentration of antibiotic under test;

c) Image Subtraction—to isolate the areas of change between two images taken at different time intervals;

d) Image Equalization—to amplify the magnitude of the changes appearing in the subtracted image;

e) Image Blurring—to reduce the effects of single pixel noise in the equalized image (low pass filter);

f) Image Contrast and Brightness Enhancement—to further amplify localized differences in the filtered image; and/or g) Inhibition Zone Detection, Measurement, and Inspection—to determine the susceptibility of microbial organisms to a particular antibiotic.

Figure 7A:
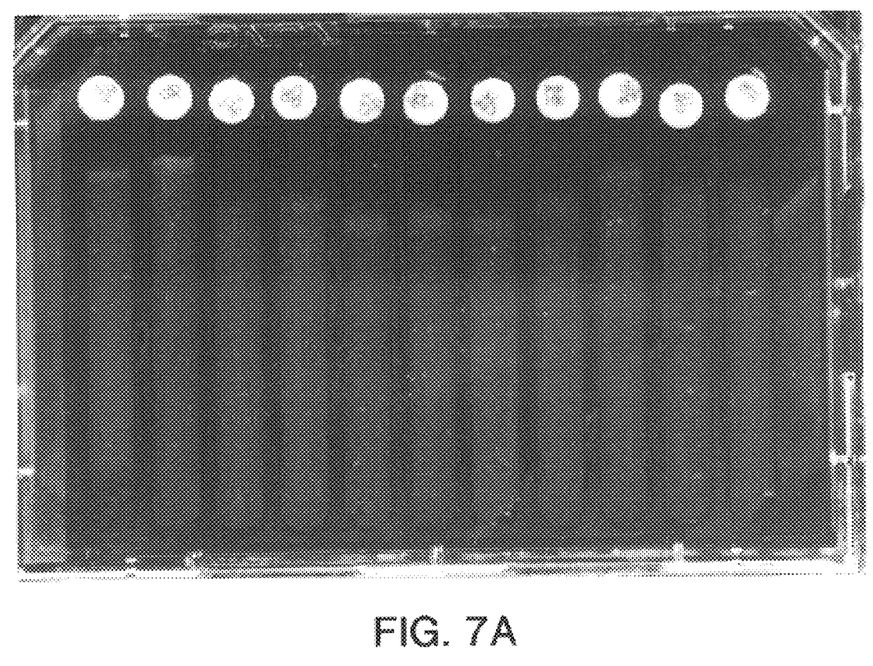
Figure 7B:
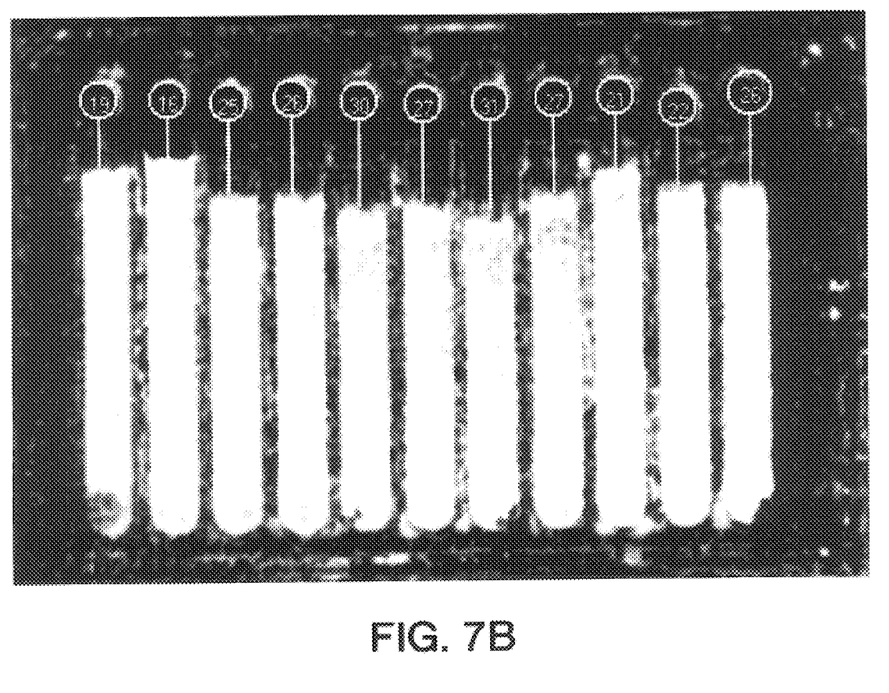
Figure 8A:
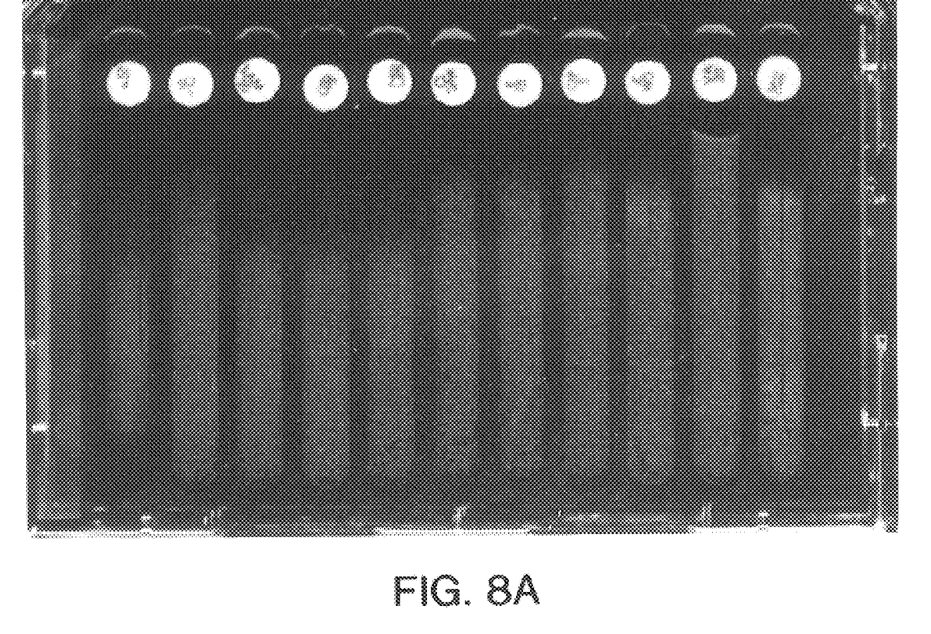
Figure 8B:
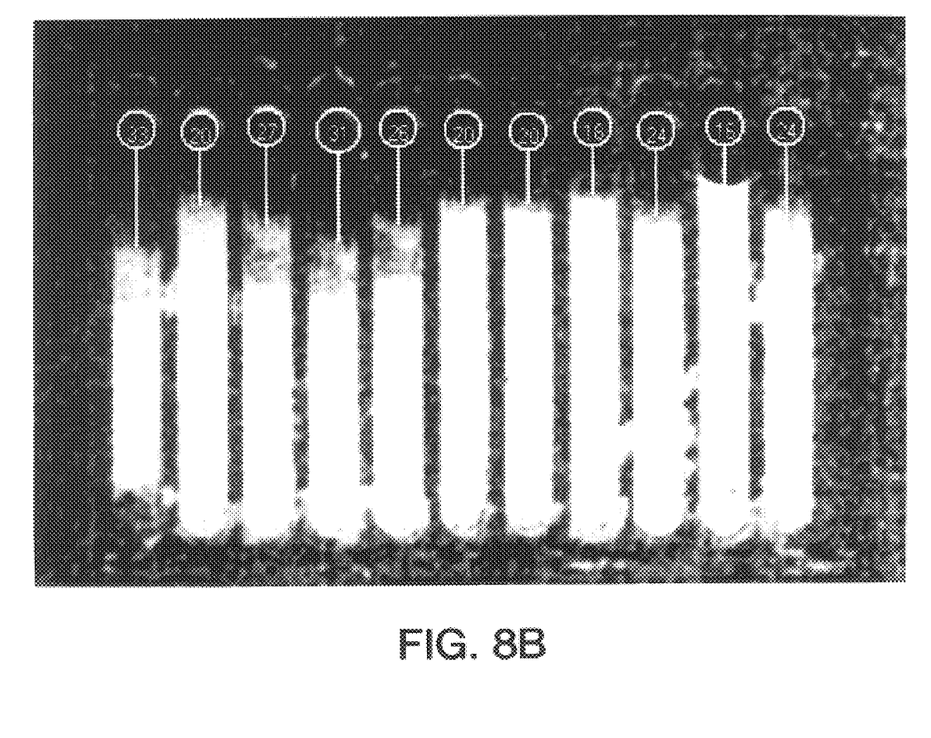

Results of susceptibility testing with system of the present invention are shown in FIGS. 7–9. FIG. 7a shows a grayscale image of *E. coli* on a susceptibility plate (using several different antibiotic disks) taken 18 hours after inoculation and antibiotic disk placement. FIG. 7b is the same plate image after image processing. The image taken at inoculation was subtracted from the image taken after 18 hours of incubation, the difference image was histogram equalized and blurred, and the zone measurement algorithm was applied to the resulting image. Inhibition zones and equivalent diameter measurements are shown in FIG. 7b. Similarly, FIGS. 8a and 8b show a grayscale image and processed image for S. aureus using the same timing and processing techniques as for FIG. 7.

Figure 9A:
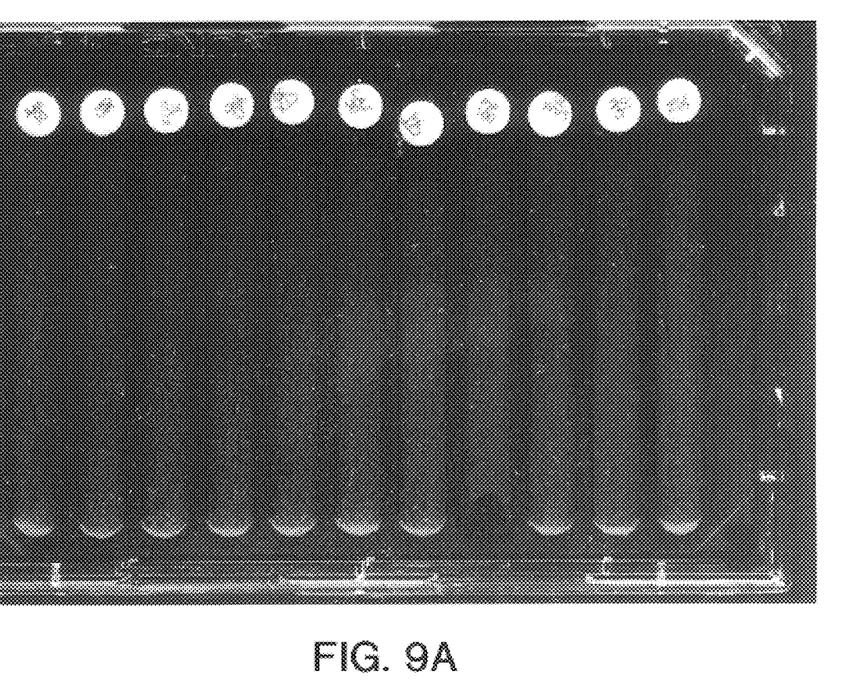
Figure 9B:
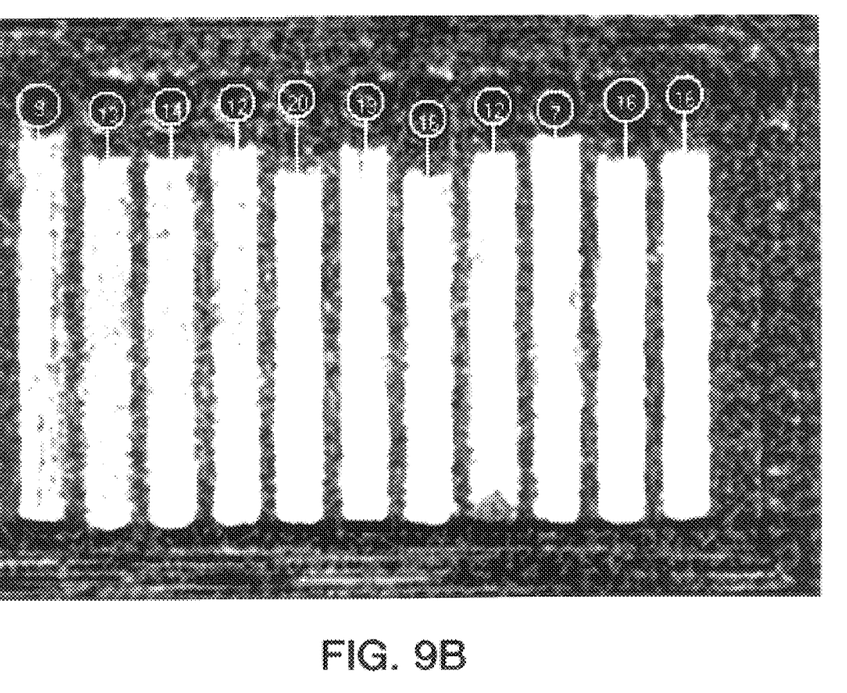
Figure 9C:
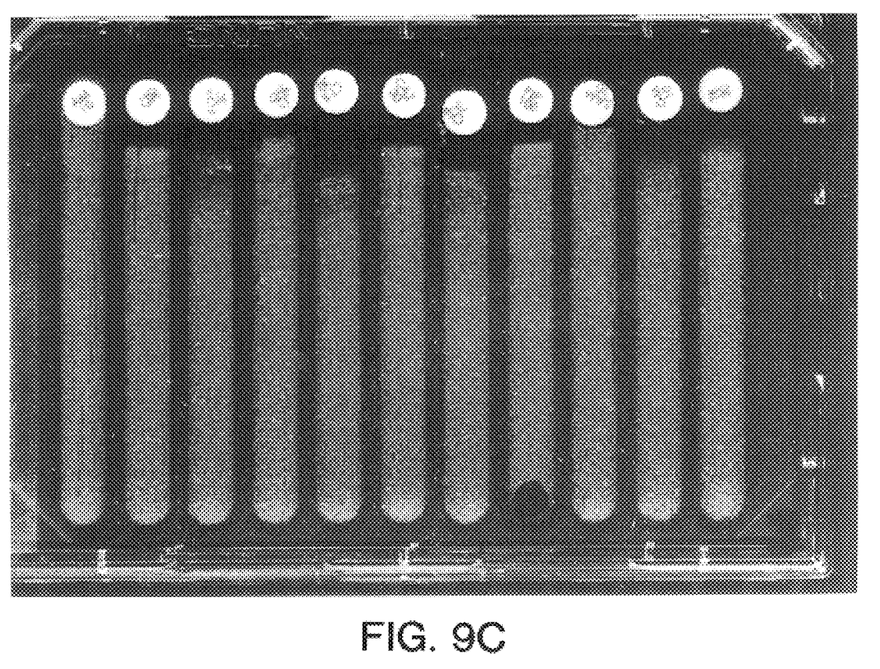
Figure 9D:
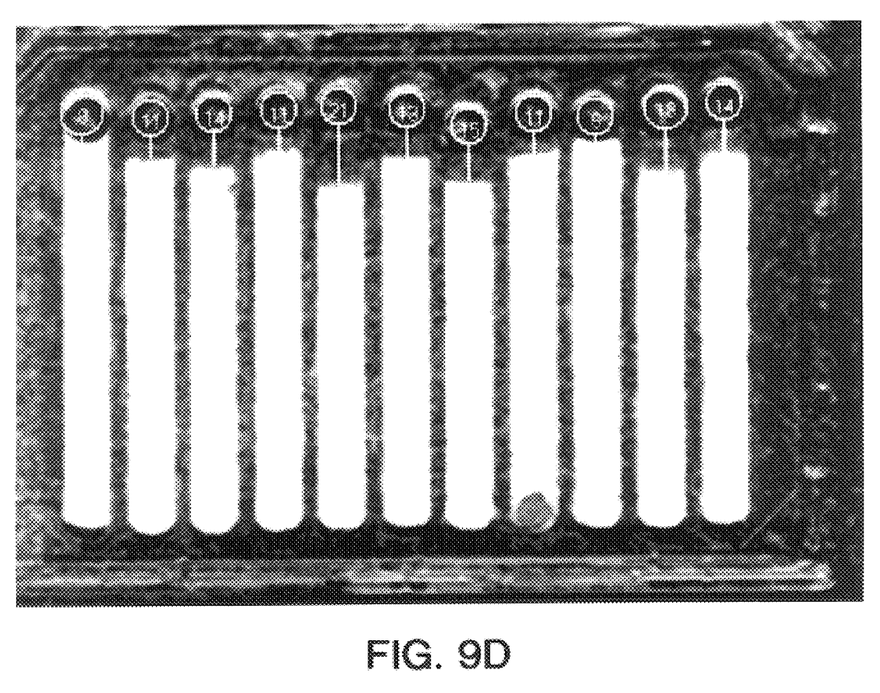

Analyses of images acquired each hour from 1 to 17 hours after inoculation demonstrate the presence of additional information regarding the interaction between the microorganisms and the antibiotics. Properties such as the growth rates of the microorganisms, the diffusion rate of the antibiotics, and the characteristics of the antimicrobial effect on the microorganism are evident. In fact, in a number of instances, the inhibition zones are defined as early as 4 to 6 hours after plate inoculation and using image processing. As an example, FIGS. 9a and 9b show a grayscale image and processed image, respectively, of Kleb. pneumoniae only four hours after inoculation (FIGS. 9c and 9d are grayscale and processed images, respectively, of the same plate after 18 hours).

The invention is also envisioned as comprising a top plate and a bottom plate where the bottom plate is a single chamber filled with the solid or semi-solid nutrient medium for the microorganisms and the top plate is provided with a plurality of ribs or dividers. When the top and bottom plates are fitted together (after placement of antibiotic discs within the "chambers" of the top plate) the nutrient medium is separated into isolated chambers as in the embodiment of the invention illustrated in FIG. 4. Of course, the ribs or dividers could be provided as a separate element from the top plate.

Another aspect of the invention is, rather than determining susceptible, intermediate or resistant, the determination of the MIC. In the present invention, MICs can be determined using a regression analysis of the zone measurement (the length of inhibition along the channel), as the diffusion of antibiotic out of the disk forms a highly predictable logarithmic gradient. Determining the MIC from the length of the disk diffusion can be performed by any known method, such as that of BIOMIC™ System by Giles Scientific (N.Y.).

In accordance with the invention, the antimicrobial agent can be applied to a plurality of compartments in differing concentrations. The solid or semi-solid growth medium should be sufficiently solid so that the antimicrobial agent when applied to the growth medium, will diffuse over time and form a concentration gradient (the concentration gradient can be formed in a horizontal direction and can continue to diffuse over a period of up to 10 to 18 hours or more). The solid or semi-solid growth medium in each chamber of the susceptibility plate is inoculated (e.g., swabbed) with a McFarland 0.5 standardized suspension of the microorganism being tested. If the microorganism is a bacterium, it can be an aerobic gram-positive organism, aerobic gram negative organism, anaerobic gram positive organism, anaerobic gram negative organism or a cell wall deficient organism.

The solid or semi-solid growth medium may comprise one or more of routine media, selective media, differential media, selective-differential media, enriched media, susceptibility media, anaerobic media and fungal media. If the media is routine media, it can comprise one or more of trypticase soy blood agar, trypticase soy agar, tryptic soy, BHI blood agar, BHI agar, Casman blood, HBT bi-layer media, and standard methods agar. If the media is selective media, it can comprise one or more of, columbia CNA blood, azide blood agar, chocolate selective, Brucella blood, blood SxT, Strep selective I & II, PEA, Bile Esculin agar, Clostridium diffiicle agar, skirrow, CCFA, CLED, Pseudomonas cepacia agar, SxT blood agar, TCBS agar, CIN, Moraxella catarrhalis media, and charcoal selective. If the media is differential media, it can comprise one or more of brilliant green, CYE—Legionella, centrimide, DNA-se, hektoen enteric agar, Jordans tartrate, mannitol salt, LIA, TSI, FLO—Pseudomonas F, TECH—Pseudomonas P, Sellers, starch agar, thermonuclease, Tinsdale agar, McCarthy, LSM, sorbitol-McConkey, MUG-McConkey.

If the media is selective and differential media, it can comprise one or more of MacConkey, EMB, Baird Parker, BHI blood with antibiotics, BiGGY—mycologic, CIN, Clostridium difficile agar, McBride, Pseudomonas isolation agar, S-S agar, turgitol 7, and XLD agar. If the media is enriched media, it can comprise one or more of chocolate, GC chocolate, BHI chocolate, Borget Gengou, heart infusion agar, McCarthy, Regan-Lowe, Thayer-Martin, transgrow medium, cysteine tellurite blood, cysteine tellurite heart, BHT, heart infusion, Loefflers, and serum tellurite. If the media is anaerobic media, it can comprise one or more of columbia base, PEA, CAN, LKV, BBE, Brucella, BHI blood base, KBE, McClung-Toabe, oxgall, Schaedlers, and Wilkens-Chalgren. And, if the media is a fungal media, it can comprise one or more of BHI base, BiGGY, birdseed, corn meal, cotton seed, DTM, sabourauds dextrose, Fuji medium, inhibition mold, Littman oxgall, mycologic, mycophil, Nickersons, SABHI, and trichophytin.

The antimicrobial agents can be one or more of a beta-lactam antibiotic, a cepheme antibiotic, a glycopeptide antibiotic, an aminoglycoside antibiotic, a macrolide antibiotic, a tetracycline antibiotic, and a quinalone antibiotic. If the antimicrobial agent is a beta-lactam antibiotic, it can comprise one or more of penicillins, uredopenicillins, synthetics, carbapenems and beta-lactam/inhibitors. If it is a cepheme antibiotic, it can comprise one or more of cephalosporins generations I to IV, and carbacephems. Also, the one or more antimicrobial agent can comprise one or more of sulfa agents and derivatives, chloramphenicol, clindamycin, nitrofurantoins, polymyxins and chemical agents.

The foregoing description is sufficient to enable one skilled in the art to practice the invention. The examples herein should not be construed as limiting the scope of the claims in any way. Indeed, various modifications of the invention in addition to those shown and described herein will become apparent to those skilled in the art from the foregoing description and fall within the scope of the appended claims.

We claim:

1. A method for determining the existence and/or degree of resistance of a microorganism to one or more antimicrobial agents, each at one or more concentrations, comprising:
   providing a container having a plurality of separate compartments, each compartment having therein a solid or semi-solid microbial growth medium;
   adding a microorganism to one or more of said separate compartments;
   placing an antimicrobial agent onto a surface of, or into, the microbial growth medium in one or more of said plurality of separate compartments;
   incubating before and/or after said placing step, said container having said microorganism and antimicrobial agent in at least one compartment thereof; and
   determining the existence and/or extent of resistance of said microorganism to said antimicrobial agent based on the existence and/or size of the inhibition zone in said compartment.

2. The method according to claim 1, wherein the determination of the existence and/or extent of resistance of said microorganism is a determination of susceptible, intermediate or resistant.

3. The method according to claim 2, wherein the determination of susceptible, intermediate or resistant corresponds at least 80% of the time with the determination made with the same microorganism and antimicrobial agent in a standard Kirby-Bauer disk diffusion method performed in accordance with NCCLS standards.

4. The method according to claim 3, wherein the correspondence is more than 90% of the time.

5. The method according to claim 1, wherein said separate compartments are elongated compartments.

6. The method according to claim 5, wherein adjacent one or more of said elongated compartment are provided markings for aiding measurement of microbial growth in the adjacent compartment.

7. The method according to claim 1, wherein said solid or semi-solid growth medium comprises one or more of routine media, selective media, differential media, selective-differential media, enriched media, susceptibility media, anaerobic media and fungal media.

8. The method according to claim 1, wherein the microorganism is a bacterium and is selected from the group consisting of aerobic gram positive organisms, aerobic gram negative organisms, anaerobic gram positive organisms, anaerobic gram negative organisms, and cell wall deficient organisms.

9. The method according to claim 1, wherein one or more antimicrobial agents are applied in one or more concentrations to the solid or semi-solid growth medium in the plurality of compartments of said container.

10. The method according to claim 1, wherein a minimum inhibitory concentration (MIC) of the antimicrobial agent for the microorganism is determined.

11. The method according to claim 10, wherein the MIC is determined by regression analysis.

12. The method according to claim 1, wherein for the same, the antimicrobial agent is applied to a plurality of compartments in differing concentrations.

13. The method according to claim 9, wherein the one or more antimicrobial agents comprise one or more of a betalactam antibiotic, a cepheme antibiotic, a glycopeptide antibiotic, an aminoglycoside antibiotic, a macrolide antibiotic, a tetracycline antibiotic, and a quinalone antibiotic.

14. The method according to claim 1, wherein said solid or semi-solid growth medium is sufficiently solid so that the antimicrobial agent when applied to the growth medium, will diffuse over time and form a concentration gradient.

15. The method according to claim 1, said step of determining the existence and/or degree of susceptibility of said microorganism to said antimicrobial agent, comprises capturing an image of said compartments of said container at one or more intervals with at least one image capture device, and determining the length of the inhibition zone within each compartment.

16. The method according to claim 15, wherein said image capture occurs at intervals of between 5 minutes to 4 hours.

17. The method according to claim 15, wherein said image capture device is comprised of one or more color and/or gray scale imaging devices.

18. The method according to claim 17, wherein said one or more color and/or gray scale imaging devices comprises a CCD linear array scanner, a CCD line-scan camera, a still CCD 2D array camera, a motion video CCD 2D array camera or a laser scanning camera.

19. The method according to claim 17, wherein a plurality of containers having said plurality of compartments and solid or semi-solid growth media are provided, and wherein said plurality of plates are manually or automatically moved relative to the image capture device and sufficiently close to the image capture device so that an image of each of the containers can be captured.

20. The method according to claim 19, wherein images of both the top and bottom of the containers are captured by one or more image capture devices.

21. The method according to claim 19, wherein said image capture device is moved to be adjacent each container.

22. The method according to claim 19, wherein each container is moved to be adjacent to the image capture device.

23. The method according to claim 15, further comprising one or more of:
  a) image masking for isolating area to be measured from extraneous image data;
  b) antimicrobial agent detection for determining the identity and/or concentration of the antimicrobial agent being tested;
  c) image subtraction for isolating areas of change between two images taken at different time intervals;
  d) image equalization for amplifying a magnitude of changes appearing in a subtracted image;
  e) image blurring for reducing effects of single pixel noise in an equalized image;
  f) image contrast and brightness enhancement for amplification of localized differences; and
  g) inhibition zone detection, measurement and inspection, for determining the susceptibility of the microorganism to the antimicrobial agent.

24. The method according to claim 1, wherein the separate compartments are elongated compartments having a length greater than about 8 mm.

25. The method according to claim 24, wherein the length is between about 20 to about 45 mm.

26. The method according to claim 24, wherein the separate compartments have a width greater than about 6 mm.

27. The method according to claim 26, wherein the width is from about 8 to about 16 mm.

28. The method according to claim 19, wherein both the containers and the image capture device are moved so that each container can be positioned adjacent the image capture device.

29. The method according to claim 16, wherein said interval is between one-half and two hours.

30. The method according to claim 5, wherein the elongated compartments are provided parallel to each other.

31. The method according to claim 10, wherein the minimum inhibitory concentration is determined by a plurality of concentrations of an antimicrobial agent on a substrate.

32. The method according to claim 1, wherein the determination of the existence and/or degree of resistance of said microorganism to said antimicrobial agent includes analysis of kinetic growth data of the microorganism provided by multiple images taken by said one or more image capture devices over time.

33. The method according to claim 7, wherein said routine media comprises one or more of trypticase soy blood agar, trypticase soy agar, tryptic soy, BHI blood agar, BHI agar, Casman blood, HBT bi-layer media, and standard methods agar.

34. The method according to claim 7, wherein said selective media comprises one or more of, columbia CNA blood, azide blood agar, chocolate selective, Brucella blood, blood SxT, Strep selective I & II, PEA, Bile Esculin agar, *Clostridium difficile* agar, skirrow, CCFA, CLED, *Pseudomonas cepacia* agar, SxT blood agar, TCBS agar, CIN, *Moraxella catarrhalis* media, and charcoal selective.

35. The method according to claim 7, wherein said differential media comprises one or more of brilliant green, CYE—Legionella, centrimide, DNA-se, hektoen enteric agar, Jordans tartrate, mannitol salt, LIA, TSI, FLO—Pseudomonas F, TECH—Pseudomonas P, Sellers, starch agar, thermonuclease, Tinsdale agar, McCarthy, LSM, sorbitol-McConkey, MUG-McConkey.

36. The method according to claim 7, wherein said selective and differential media comprises one or more of MacConkey, EMB, Baird Parker, BHI blood with antibiotics, BiGGY—mycologic, CIN, *Clostridium Difficile* agar, McBride, Pseudomonas isolation agar, S—S agar, turgitol 7, and XLD agar.

37. The method according to claim 7, wherein said enriched media comprises one or more of chocolate, GC chocolate, BHI chocolate, Borget Gengou, heart infusion agar, McCarthy, Regan-Lowe, Thayer-Martin, transgrow medium, cysteine tellurite blood, cysteine tellurite heart, HBT, heart infusion, Loefflers, and serum tellurite.

38. The method according to claim 7, wherein said anaerobic media comprises one or more of columbia base, PEA, CAN, LKV, BBE, Brucella, BHI blood base, KBE, McClung-Toabe, oxgall, Schaedlers, and Wilkens-Chalgren.

39. The method according to claim 7, wherein said fungal medium comprises one or more of BHI base, BiGGY, birdseed, corn meal, cotton seed, DTM, sabourauds dextrose, Fuji medium, inhibition mold, Littman oxgall, mycologic, mycophil, Nickersons, SABHI, and trichophytin.

40. The method according to claim 13, wherein the beta-lactam antibiotic comprises one or more of penicillins, uredopenicillins, synthetics, carbapenems and beta-lactam/inhibitors.

41. The method according to claim 13, wherein the cepheme antibiotic comprises one or more of cephalosporins generations I to IV, and carbacephems.

42. The method according to claim 9, wherein the one or more antimicrobial agents comprises one or more of sulfa agents and derivatives, chloramphenicol, clindamycin, nitrofurantoins, polymyxins and chemical agents.

43. The method according to claim 1, wherein the solid or semi-solid growth medium is provided in each compartment at a depth of greater than 1 mm.

44. The method according to claim 43, wherein the depth of the growth medium is from about 2 mm to about 15 mm.

45. The method according to claim 44, wherein the depth of the growth medium is from about 5 mm to about 15 mm.

46. The method according to claim 1, wherein the microorganism is a bacterium, fungus, protozoa, algae or virus.

47. The method according to claim 1, wherein said separate compartments are formed upon assembly of the container and after addition of said microorganism and growth medium.

48. A kit for determining the existence and/or degree of resistance of a microorganism to one or more antimicrobial agents, each at one or more concentrations, comprising:

one or more antimicrobial agents provided on substrates;

a container having a plurality of separate compartments, at least when assembled;

growth medium within said container or for adding to said container, said growth medium when in said container forming a solid or semi-solid growth medium and said growth medium being sufficiently solid so that the antimicrobial agent when applied to the growth medium will diffuse over time and form a concentration gradient.

49. A method for determining the existence and/or degree of resistance of a microorganism to one or more antimicrobial agents each at one or more concentrations, comprising:

providing a container having a plurality of separate compartments, each compartment having therein a solid or semi-solid microbial growth medium for growth of a microorganism to be tested for antimicrobial susceptibility, and for a corresponding antimicrobial agent;

adding a sample containing microorganisms to a respective compartment containing solid or semi-solid microbial growth medium;

placing an antimicrobial agent onto said solid or semi-solid microbial growth medium;

incubating said container having said microorganism and antimicrobial substance in at least one compartment thereof; and determining the existence and/or the degree of resistance of said microorganism to said antimicrobial agent based on the existence and/or size of the inhibition zone in said compartment.

* * * * *